US008767202B2

(12) United States Patent
Schmidt et al.

(10) Patent No.: US 8,767,202 B2
(45) Date of Patent: Jul. 1, 2014

(54) SERS SUBSTRATE AND A METHOD OF PROVIDING A SERS SUBSTRATE

(75) Inventors: Michael Stenbaek Schmidt, Copenhagen SK (DK); Anja Boisen, Birkerød (DK); Jörg Hübner, Aalsgaarde (DK)

(73) Assignee: Danmarks Tekniske Universitet, Lyngby (DK)

( * ) Notice: Subject to any disclaimer, the term of this patent is extended or adjusted under 35 U.S.C. 154(b) by 503 days.

(21) Appl. No.: 12/911,061

(22) Filed: Oct. 25, 2010

(65) Prior Publication Data

US 2011/0116089 A1 May 19, 2011

(30) Foreign Application Priority Data

Oct. 23, 2009 (DK) .................................. 2009 01149

(51) Int. Cl.
*G01N 21/65* (2006.01)
(52) U.S. Cl.
USPC .......................................................... 356/301
(58) Field of Classification Search
USPC .......................................... 356/301; 436/165
See application file for complete search history.

(56) References Cited

U.S. PATENT DOCUMENTS

| | | | | |
|---|---|---|---|---|
| 5,017,007 | A * | 5/1991 | Milne et al. .................... | 356/301 |
| 6,623,977 | B1 | 9/2003 | Farquharson et al. | |
| 6,970,239 | B2 | 11/2005 | Chan et al. | |
| 6,989,897 | B2 * | 1/2006 | Chan et al. .................... | 356/301 |
| 7,158,219 | B2 | 1/2007 | Li et al. | |
| 7,192,778 | B2 | 3/2007 | Natan | |
| 7,321,422 | B2 | 1/2008 | Li et al. | |
| 7,342,656 | B2 * | 3/2008 | Islam et al. .................... | 356/301 |
| 7,426,025 | B2 * | 9/2008 | Wang ............................. | 356/301 |
| 7,483,130 | B2 | 1/2009 | Baumberg et al. | |
| 7,576,854 | B2 * | 8/2009 | Wang et al. .................... | 356/301 |
| 7,727,776 | B2 | 6/2010 | Zhou et al. | |
| 7,833,801 | B2 * | 11/2010 | Stasiak et al. ................. | 436/149 |
| 7,888,129 | B2 * | 2/2011 | Hulteen et al. ................. | 436/165 |
| 7,898,658 | B2 | 3/2011 | Moskovits et al. | |
| 7,960,252 | B2 * | 6/2011 | Chen ............................. | 438/478 |
| 8,048,377 | B1 * | 11/2011 | Zhou et al. .................... | 422/82.02 |
| 8,223,331 | B2 | 7/2012 | Bratkovski et al. | |
| 2003/0166297 | A1 | 9/2003 | Natan | |

(Continued)

FOREIGN PATENT DOCUMENTS

DE  10 2007 0370201   2/2009
WO  WO 99/44045      9/1999

OTHER PUBLICATIONS

International Search Report and Written Opinion dated Feb. 7, 2011 issued in corresponding International Application No. PCT/DK2010/050284.

(Continued)

*Primary Examiner* — Kara E Geisel
(74) *Attorney, Agent, or Firm* — Harness, Dickey & Pierce, P.L.C.

(57) ABSTRACT

A substrate primarily for SERS determination, the substrate has a number of elongate elements with a density of at least $1 \times 10^8$ elongate elements per $cm^2$ and having metal coated tips. When the elements may be made to lean toward each other, such as by providing a drop of a liquid thereon and allowing the liquid to dry, groups of tips of elongate elements are formed and the Raman enhancement is extremely high.

30 Claims, 9 Drawing Sheets

(56) References Cited

U.S. PATENT DOCUMENTS

| | | | |
|---|---|---|---|
| 2003/0231304 | A1 | 12/2003 | Chan et al. |
| 2005/0142567 | A1 | 6/2005 | Su et al. |
| 2006/0054881 | A1 | 3/2006 | Li et al. |
| 2006/0055922 | A1 | 3/2006 | Li et al. |
| 2006/0119853 | A1 | 6/2006 | Baumberg et al. |
| 2006/0164634 | A1 | 7/2006 | Kamins |
| 2007/0153267 | A1 | 7/2007 | Wang |
| 2008/0024776 | A1* | 1/2008 | Bratkovski et al. ............ 356/301 |
| 2008/0094621 | A1* | 4/2008 | Li et al. ......................... 356/301 |
| 2008/0096289 | A1 | 4/2008 | Zhou et al. |
| 2008/0174775 | A1* | 7/2008 | Moskovits et al. ........... 356/301 |
| 2009/0122310 | A1 | 5/2009 | Zhang et al. |
| 2009/0218028 | A1 | 9/2009 | Wang |
| 2009/0298197 | A1 | 12/2009 | Natan et al. |
| 2010/0284001 | A1 | 11/2010 | Moskovits et al. |

OTHER PUBLICATIONS

Michael S. Pio et al., "Batch Fabrication of Nanopillars for Autonomous Nanofluidic SERS Arrays", *Mat. Res. Coc. Symp. Proc.*, vol. 729, pp. U4.9.1-U.4.9..6 (2002).

Jing Tang et al., "Silver-coated Si nanograss as highly sensitive surface-enhanced Raman spectroscopy substrates", *Appl. Phys A*, vol. 96, No. 4, pp. 793-797 (Jun. 27, 2009).

Min Hu et al., "Metal Coated Si Nanograss as Highly Sensitive SERS Sensors",*Proc. of SPIE*, vol. 7312, (Apr. 13, 2009).

Kim, A. et al. "Study of Molecular Trappings Inside Gold Nanofinger Arrays on Surface-Enhanced Raman Substrates," *Journal of American Chemical Society*, 2011, vol. 133, p. 8234-8239.

M. G. Albrecht and J. A. Creighton, "Anomalously intense Raman-spectra of pyridine at a silver electrode," J. Am. Chem. Soc., 99 (15), 1977, pp. 5215-5217.

D. L. Jeanmaire and R. P. Van Duyne, "Surface Raman spectroelectrochemistry .1. heterocyclic, aromatic, and aliphatic-amines adsorbed on anodized silver electrode," J. Electroanal. Chem., vol. 84 (1), 1977, pp. 1-20.

H. Wang, C.S. Levin and N. J. Halas, "Nanosphere arrays with controlled sub-10-nm gaps as surface-enhanced Raman spectroscopy substrates," J. Am. Chem. Soc., vol. 127 (43), 2005, pp. 14992-14993.

F. Le, D.W. Brandl, Y.A. Urzhumov, H. Wang, J. Kundu, N.J. Halas, J. Aizpurua and Peter Nordlander, "Metallic nanoparticle arrays: a common substrate for both surface-enhanced Raman scattering and surface-enhanced infrared absorption," Am. Chem. Soc. Nano, vol. 2 (4), 2008, pp. 707-718.

K. Kneipp, Y. Wang, H. Kneipp, L.T. Perelman, I. Itzkan, R. Dasari and M.S. Feld, "Single molecule detection using surface-enhanced Raman scattering (SERS)," Phys. ReV. Lett., vol. 78 (9), 1997, pp. 1667-1670.

F. Yan, M.B. Wabuyele, G.D. Griffin, A.A. Vass and T. Vo-Dinh, "Surface-enhanced Raman scattering detection of chemical and biological agent simulants," IEEE Sensors Journal, vol. 5 (4), 2005, p. 665-670.

E.C. Le Ru, P.G. Etchegoin, J. Grand, N. Félidj, J. Aubard, G. Lévi, A. Hohenau and J.R. Krenn, "Surface enhanced Raman spectroscopy on nanolithography-prepared substrates", Current Applied Physics 8, 2008, pp. 467-470.

I. Talian, K.B. Mogensen, A. Oriňák, D. Kaniansky and J. Hübner, "Surface-enhanced Raman spectroscopy on novel black silicon-based nanostructured surfaces", Journal of Raman Spectroscopy, 2009, DOI 10.1002/jrs.2213.

Klarite™: http://www.d3technologies.co.uk.

M.S. Schmidt, T. Nielsen, D.N. Madsen, A. Kristensen and P. Bøggild, "Nanoscale silicon structures by using carbon nanotubes as reactive ion etch masks", Nanotechnology, vol. 16, 2005, pp. 750-753.

A. Gopinath, S.V. Boriskina, B.M. Reinhard and L.D. Negro, "Deterministic aperiodic arrays of metal nanoparticles for surface-enhanced Raman scattering (SERS)," Optics Express, vol. 17 (5), 2009, pp. 3741-3753.

Gopinath A. et al., "Photonic-Plasmonic Scattering Resonances in Deterministic Aperiodic Structures".

E. D. Diebold, N. H. Mack, S. K. Doorn and E. Mazur, "Femtosecond laser-nanostructured substrates for surface enhanced Raman scattering," Langmuir, vol. 25 (3), 2009, pp. 1790-1794.

M. Hu, J. Tang, F.S. Ou, H.P. Kuo, S.-Y. Wang, Z. Li and R.S. Williams, "Metal coated Si nanograss as highly sensitive SERS sensors," Proceedings of the SPIE, vol. 7312 (1), 2009, pp. 73120I-73120I-6.

J. Hubner, T. Anhøj, S. Pedersen, D.A.Zauner, A.M. Jørgensen, G. Blagoi, I. Talian and O. Hansen, "Surface enhanced Raman spectroscopy on chip," Proceedings of the SPIE—Integrated Optics: Devices, Materials, and Technologies XII, vol. 6896, 2008, pp. 689614-1-698614-10.

Aizenberg J. et al., "Control of Shape and Size of Nanopillar Assembly by Adhesion-Mediated Elastocapillary Interaction".

Driskell et al., "The use of Aligned Silver Nanorod Arrays Prepared by Oblique Angle Deposition as Surface Enhanced Raman Scattering Substrates".

Gartia, M.R. et al., "Rigorous surface enhanced Raman spectral characterization of large-area high-uniformity silver-coated tapered silica nanopillar arrays".

Hu, M. et al., "Gold Nanofingers for Molecule Trapping and Detection".

Hu, M. et al., "Nano gold fingers for molecule trapping and detection".

Hu, Y.S. et al., "Enhanced Raman Scattering from Nanoparticle-Decorated Nanocone Substrates: A Pratical Approach to Harness In-Plane Excitation".

Leng W. et al., "Silver Nanocrystal-Modified Silicon Nanowires as Substrates for Surface-Enhanced Raman and Hyper-Raman Scattering".

Liz-Marzan L. et al., Chemical seeded growth of Ag nanoparticle arrays and their application as reproducible SERS substrates.

Mao H.Y. et al., "Silicon nanopillar-forest based microfluidic surface-enhanched raman scattering devices".

Fan M. et al., "Silver nanoparticles self assembly as SERS substrates with near single molecule detection limit".

Tang J. et al., Metallic nanocrystals near ultrasmooth metallic films surface-enchanted Raman scattering application.

Tang J. et al., Poster: "Metallic Nanocrystals Near Ultra-smooth Metallic Film for SERS Application".

Tang J. et al., "Silver-coated Si Nanograss as highly sensitve surface-enhanced Raman spectroscopy substrates".

Theiss J. et al., "Plasmonic Nanoparticle Arrays with Nanometer Separation for High-Performance SERS substrates".

Vo-Dinh, T. et al., "Plasmonic Nanoparticle and Nanowires: Design, Fabrication and Application in Sensing".

Wang, Y. et al., "Nanostructured Gold Films for SERS by Block Copolymer-Templated Galvanic Displacement Reactions".

Wu W. et al.: "Rational Engineering of Highly Sensitive SERS Substrates Based on Nanocone Structures".

Schmidt M. S. et al., "Easily fabricated nano-structured SERS sustrates with large enhancement", ETH Bio-plasmonics 2010, Apr. 18, 2010.

Schmidt M. S. et al., "Two-Step Fabrication of Metal-Coated Silicon Nanopillars with Large Raman Enhancement", ICORS 2010, Aug. 8, 2010.

Schmidt M. S. et al., "Towards Easily Reproducible Nano-structured SERS Substrates", IEEE Sensors 2009 Proceedings, Oct. 25, 2009.

Schmidt M. S. et al., "Metal-coated silicon nanopillars with large Raman enhancement for explosives detection", SPIE Defense 2010 proceedings, Apr. 6, 2010.

\* cited by examiner e f

Outside droplet area
No leaning

Inside droplet area
Pillar leaning g Inside droplet area - Pillar leaning

Outside droplet area
No leaning

SERS SUBSTRATE AND A METHOD OF PROVIDING A SERS SUBSTRATE

CROSS-REFERENCE TO RELATED APPLICATIONS

This application claims priority under 35 U.S.C. §119 from Danish Patent Application No. PA 2009 01149, filed on Oct. 23, 2009, in the Danish Intellectual Property Office, the disclosure of which is incorporated herein in its entirety by reference.

The present invention relates to a new SERS substrate and a method of manufacturing or providing the SERS substrate. In particular, the invention relates to a SERS substrate having a plurality of nanopillars with a density and an aspect ratio allowing bending of the nanopillars to form groups of tips thereof positioned within 20 nm or less and thus forming highly efficient hot spots there between.

Surface Enhanced Raman Scattering (SERS) spectroscopy was discovered in 1974 and is now a powerful analysis technique which is becoming more widespread due to the development of cheaper lasers and spectrometer systems. SERS derives information about the type of chemical bonds in trace amounts of analyte molecules when these are adsorbed onto, or placed adjacent to, a metal surface or structure: a so-called SERS substrate. As it is vibrations in the chemical bonds of the analyte that result in the Raman spectrum, any chemical and molecular species can in theory be identified. For this reason SERS has shown great potential of becoming a versatile analytical tool for both chemical and biochemical sensors in liquid and gas phases.

SERS is based on laser excitation inducing an electromagnetic field at the surface of noble metals. Areas with particularly large electromagnetic fields, also called "hot spots", are found in between adjacent metal nano structures or nano particles, if these are located sufficiently close to each other, i.e. on the order of a few nm. If an analyte molecule is located inside this hot spot it will result in a relatively large Raman signal from the analyte. Recent studies have shown that hot spots account for an inproportionally large contribution to the total Raman signal collected from a SERS substrate.

Ideally, a SERS substrate should both enhance the Raman effect in order to enable suitable chemical detection levels and at the same time be practical to use in a sensor system. Broadly speaking, SERS substrates can be classified into two categories, a) Metallic nano particles in colloidal solution and b) roughened metallic or metal coated surfaces. Due to the wide range of obtainable sizes and shapes of metal nano particles colloidal suspensions of metallic nano particles are attributed to having the largest enhancement factors. Furthermore, single molecule detection with SERS has been demonstrated with colloidal suspensions of gold nano particles. However, with colloid solutions it is a challenge to bring the metal nano particles sufficiently close to each other to form hot spots, while at the same time preventing large conglomerations of nano particles from forming before the analyte is introduced. Rough silver and gold surfaces can be manufactured by a number of methods including chemical etching, mechanical deformation, electroplating and oblique angle deposition. Lately, processes where well defined silicon nanostructures are created, by for example electron beam lithography, and hereafter covered by thin films of gold or silver have shown promising results. However this approach has a very high manufacturing cost and is generally unfeasible for areas above a couple of mm$^2$.

Currently, the inability to mass produce large areas of cost effective nano structured SERS-substrates with large numbers of hot spots and hence suitable Raman enhancement is impeding the use of SERS sensors in both laboratories and mobile applications.

Thus, it is an object of the invention to provide a SERS substrate which combines the advantages of both colloidal metal nano particles and solid surfaces to achieve large Raman enhancements which are reproducible over large areas (wafer scale) and from wafer to wafer.

In a first aspect, the invention relates to a substrate comprising:
  a base and
  a plurality of elongate elements extending from the base,
    each element having a tip positioned at one end away from the base, at least one tip having a metallic surface,
  the elements being positioned, at the base, with a density of at least $1\times10^8$ elongate elements per cm$^2$.

In the present context, a substrate may be any type of element. The substrate may be made of any material or combination of materials. The substrate has, due to the elongate elements with metallized tip(s) a surface which may be used for e.g. SERS measurements. This is described further below.

In the present context, the base preferably is a plane base, as this is the easiest base to provide the elongate elements on. However, the base may have any shape or thickness and may be made of any material. In e.g. SERS measurements, the base has virtually no influence, so the construction of the base is, in that respect, not important.

In the present context, an elongate element is an element which has a longest dimension, along a longitudinal axis, extending away from the base. Preferably, all elongate elements extend away from the base in at least substantially the same direction. The elongate element has a thickness perpendicular to the longitudinal axis.

It is noted that the elongate elements may be provided on, such as fixed to or grown on, the base or may have been made by removing material from an initial substrate, so that the base and elongate elements are one monolithic element.

Naturally, if the area of the substrate or base at which the elongated elements are positioned is less than 1 cm$^2$, the density may be determined for smaller areas. One manner of determining the density is to outline a surface from which the elongated elements extend, determine the area thereof and determine the number of elongate elements therein, such as the number of elongate elements which, within the area, contact, engage, are attached to, are fixed to or otherwise touch the base/substrate within the area. Below, a substrate is described which has elongate elements which bend. In this situation, the tips of elongate elements may extend outside of the area, but the elongate elements still extend from within the area.

Preferably more than a single tip has a metallic surface or another surface which is suitable for e.g. SERS substrates. Actually, preferably at least 10%, such as at least 30%, preferably at least 50%, such as at least 75%, preferably at least 90%, such as at least 99% of the tips have a metallic surface.

In this context, a metallic surface is a surface at least substantially covering the tip of the elongate element. The tip being the part of the elongate element being the farthest from the base along the longitudinal axis. The metallic surface need not cover any part of the elongate element between the tip and the base. However, depending on the thickness and manner of deposition of the metallic layer, 1% or more, such as 2% or more, such as 5%, 10%, 20%, 40% or more of the length of the elongate element, between the base and the tip, may be covered by a metallic layer. The metallic layer may be an even layer or an uneven layer.

Even though it is desired that the layer on a tip of an elongate element fully covers the tip, production imperfections may occur whereby a percentage of the tip is not covered.

It is noted that the metallic layer of each tip preferably is separate from the metallic layer of other tips. Thus, each tip is able to move independently of others, at least before the below mentioned leaning.

Preferably, a layer thickness of the metallic surface is 5 nm or more, such as 10 nm or more, preferably 25 nm or more, such as 40 nm or more. In one situation, the layer thickness is no more than 35%, such as no more than 30%, preferably no more than 25%, such as no more than 20% of a mean distance/spacing between elongate elements at the base. In this situation, the tips are separate and may move separately from each other.

It is noted that the providing of the metallic surface may also be obtained by providing the elongated element(s) of the same metal. Thus, providing all elongated elements of the desired metal automatically provides elongated elements with tips with the desired surface.

Preferably, an elongate element has a height, along a longitudinal direction thereof, of at least 30 nm, such as at least 40 nm, preferably at least 50 nm, such as at least 100 nm, preferably at least 200 nm, such as at least 400, 500, 600, 700, 1000, 1200, 1400 or 1600 nm.

In one situation, an elongate element, or preferably more than 10, 20, 30, 40, 50, 60, 70, 80, 90 or 95% of the elongate elements, preferably has/have a height being at least 2 times a mean spacing between the elongated elements. The mean spacing may be determined from the density of elongated elements, such as by assuming that the elongated elements are positioned in a perfect pattern on the base, such as in straight columns and rows.

In that or another situation, an elongate element, or preferably more than 10, 20, 30, 40, 50, 60, 70, 80, 90 or 95% of the elongate elements, has/have a ratio between a height along the longitudinal axis thereof and a mean width thereof of at least 5, such as at least 6, at least 7, at least 8, at least 9, at least 10, at least 15 or at least 20. In this respect, the mean width of the elongate element is the mean width measured between the tip and the base excluding any metal layer or surface.

In one situation, a majority of the elongate elements, i.e. at least 50%, such as at least 60%, preferably at least 70%, such as at least 80%, preferably at least 90% or 95% of the elongate elements, have a height within 20%, such as within 10%, preferably within 5%, of a mean height of the majority of the elongate elements. In this manner, the tips will be within at least substantially the same height also when leaning (see below). If the tips are positioned in at least substantially the same plane, it will be easier to e.g. focus a laser beam thereon when performing a SERS measurement. In addition, when the tips are in at least substantially the same height before leaning, the leaning tips will form hotspots as opposed to a tip leaning against a part of an elongated element with no metal surface.

In the below-mentioned leaning condition, it is desired that the elongate elements are able to firstly lean and secondly bend at a well defined position. Clearly, if one elongate element bends or primarily bends at the base and the other no more than 10% from the tip, formation of groups of tips will differ. Leaning at e.g. the base or close to the base will give the elongated element a longer "range" to form a group with other tips.

In one embodiment, the elongate element, or preferably a majority of the elongate elements, such as at least 50%, 60%, 70%, 80%, 90% or at least 95% of the elongate elements, has/have a neck portion and a tip portion, the tip portion being positioned at the tip and having a larger cross section, perpendicular to the longitudinal direction, than the neck portion which is positioned closer to the base than the tip portion, a mean width, also in the perpendicular direction, of the neck portion being no more than 80%, such as no more than 75%, such as no more than 70%, preferably no more than 65%, such as no more than 60%, 55% or 50%, of a mean width of the tip portion.

In this respect, the tip portion of the elongate element may be a part of the elongated element not having a metal coating, or it may be close to the tip and thereby have a metal coating.

Defining or providing a neck portion will aid in providing a well defined bending point or a point where an overall part of the bending takes place. Preferably, this neck portion is positioned far from the tip portion in order for the part of the elongate element between the neck portion and the tip to be as long as possible.

In that or another embodiment, at least one elongate element, but preferably each of at least 10%, 20%, 30%, 40%, 50%, 60%, 70%, 80%, 90% or at least 95% of the elongate elements, has/have a spring constant of no more than 250 N/m, such as no more than 100N/m, preferably no more than 50N/m, such as no more than 20N/m. An estimate of a 100 nm diameter 600 nm tall Si pillar is about 12.3 N/m.

In that or another embodiment, at least one elongate element, but preferably each of at least 10%, 20%, 30%, 40%, 50%, 60%, 70%, 80%, 90% or at least 95% of the elongate elements, is/are bendable, so that providing a force to the tip thereof, the force being perpendicular to the longitudinal direction, of no more than 20 µN, will make the tip move at least 50% of a height of the elongate element along the longitudinal direction, in a direction perpendicular to the longitudinal direction.

The low force makes the formation of groups possible without the risk of breaking the elongate elements, if they are too stiff.

In a particularly interesting embodiment, a number of the elongate elements lean or bend. In this situation, a plurality of groups of elongate elements exist, the tips of the elongate elements of each group being positioned within a distance of 20 nm or less, such as at least 15 nm, such as at least 10 nm, such as at least 5 nm, from each other.

In this context, a group of elongate elements is a number of elements having a tip being within 20 nm of a tip of another elongate element in the group.

It has been found that these groups of tips are especially efficient in SERS. Thus, it is desired to have as many groups or especially as many tips form part of a group as possible.

Thus, preferably, at least 25%, such as at least 35%, preferably at least 50%, such as at least 75%, of the elongated elements each form part of a group with at least 3 elongate elements.

It is clear, especially in the leaning situation, that the density of elongate elements, the sizes of the tips when covered by metal, the bendability of the elongate elements as well as where, along their lengths, the elongate elements bend, will determine the ability of forming of groups of tips.

However, it is preferred that the elongate elements are positioned, on the substrate, with a density of no more than $4 \times 10^9$ tips per cm$^2$, such as no more than $3 \times 10^9$ tips per cm$^2$, such as no more than $2 \times 10^9$ tips per cm$^2$, as a too high density makes individual metallization of the tips very difficult.

A second aspect of the invention relates to a method of transforming a substrate according to the first aspect, the method comprising forming a plurality of groups of elongate elements, the tips of the elongate elements of each group being positioned within a distance of 20 nm or less from each other. Thus, the above groups are formed.

Naturally, all embodiments and situations described above are relevant also in this aspect of the invention.

This substrate has been shown to be more suited for SERS measurements than that in which the tips are positioned and spaced approximately as the elongate elements at the base.

Preferably, the forming step comprises humidifying with a liquid and subsequently drying the elongated elements. Preferably, a number of the elongated elements, or at least the tips thereof, such as a majority of the elongated elements, such as at least 50%, 60%, 70%, 80%, 90% or at least 95% of the elongate elements, are humidified. This humidification may be the providing of a drop or amount of the liquid on the tip(s). Alternatively, the elongated elements may be cooled, and the substrate positioned in a vapour of the liquid. Other manners of humidifying are known.

It is noted that virtually any liquid may be used, as long as the drying step is adapted to the liquid to obtain the drying. No particular requirements are put on e.g. the time required for the drying to take place.

Thus, the drying step may be performed by adapting a temperature and atmosphere to the particular liquid. It may be desired to heat the elongated elements to facilitate drying, and it may be desired to lower a pressure or partial pressure (of a particular gas, for example) at the tip(s).

In addition, the drying step may comprise the step of providing nitrogen, argon other inert gases or dry air.

In another situation, the forming step comprises exerting a force to the substrate and causing adhesion of the tips to each other by surface tension, electrostatic and/or magnetic forces. This exertion of the force may be the providing of a magnetic field, mechanical vibration and/or an electrostatic field. It has been noted that simply scanning an area of elongated elements with an electron beam as in a scanning electron microscope causes the elongated elements to lean toward each other due to electrostatic charging. No charging or the like is, however, required to have the elongated elements maintain their bended positions.

A third aspect of the invention relates to a method of detecting the presence of a substance on a surface of a substrate according to the first aspect or a substrate transformed according to the second aspect, the method comprising providing radiation toward the tips and performing Raman Spectroscopy on the basis of radiation inelastically scattered by the substance.

Naturally, all embodiments and situations described in relation with the above aspects are relevant also in this aspect of the invention.

Preferably, the method further comprises the step of estimating a quantity of the substance present on the substrate on the basis of a received intensity of scattered radiation having a wavelength within one or more predetermined wavelength intervals.

Raman Spectroscopy on this type of structure is well known to the skilled person. The fact that the substrate itself has changed needs not change the manner in which the radiation is provided, detected, and the measurements used for performing the determination.

Additionally, the substance may be provided on the surface in the manners usual for Raman Spectroscopy. However, the method may further comprise the above-mentioned bending step, where the groups of tips are generated either before or after the exposure to the substance or the providing of the substance on the tips.

It is noted that the elongate elements may be pre-leaned before the substance is provided on the tips, or the elongate elements may made to bend subsequently. Also, the substrate may be used without bending the elongate elements.

A fourth aspect of the invention relates to a method for producing a substrate according to the first aspect, the method comprising:
1. providing, in or on a substrate, a plurality of elongated elements with a density of at least $1 \times 10^8$ elongate elements per $cm^2$, and
2. providing a metallic surface on at least a tip of one of the elongated elements.

As is mentioned in relation to the first aspect of the invention, the elongated elements may be of a different material or made in another process than the base and subsequently be fixed to or attached to the base. Alternatively, the base and elongated elements are made of the same material by removing parts thereof to form the elongated elements.

Also, the providing of the metallic surface may be a part of step 1. if the elongate element(s) are made of the metal in question.

The base preferably is flat.

As mentioned above, the density may be determined also for areas below 1 $cm^2$.

As mentioned above, preferably more than a single tip has a metallic surface or another surface which is suitable for e.g. SERS substrates. Actually, the step of providing the metallic surface comprises providing a metallic surface on the tips of preferably at least 10%, such as at least 30%, preferably at least 50%, such as at least 75%, preferably at least 90%, such as at least 99% of the elongated elements.

Preferably, the step of providing the metallic surface comprises providing metallic surfaces of a number of tips, which metallic surfaces are separate from each other. Thus, the metallic surfaces are not fixed to or attached to each other, so that each tip with a metallic surface is able to move independently of others, at least before the below mentioned leaning.

Preferably, a layer thickness of the metallic surface is 5 nm or more, such as 10 nm or more, preferably 25 nm or more, such as 40 nm or more. In one situation, the layer thickness is no more than 35%, such as no more than 30%, preferably no more than 25%, such as no more than 20% of a mean distance/spacing between elongate elements at the base. In this situation, the tips are separate and may move separately from each other.

Preferably, step 1 comprises providing elements with a height, along a longitudinal direction thereof, of at least 30 nm, such as at least 40 nm, preferably at least 50 nm, such as at least 100 nm, preferably at least 200 nm, such as at least 400, 500, 600, 700, 1000, 1200, 1400 or 1600 nm. As mentioned above, preferably at least 10%, 20%, 30%, 40%, 50%, 60%, 705, 80%, 90% or 95% of the elongated elements fulfil this requirement.

In that or another situation, step 1. comprises providing a majority of the elongate elements, i.e. at least 50%, such as at least 60%, preferably at least 70%, such as at least 80%, preferably at least 90% or 95% of the elongate elements, with a height within 20% of a mean height of the majority of the elongate elements.

In that or another situation, step 1. comprises providing at least one elongate element, such as at least 50%, 60%, 70%, 80%, 90% or at least 95% of the elongate elements, with a ratio between a height along a longitudinal direction thereof and a mean width thereof of at least 5, such as at least 6, at least 7, at least 8, at least 9, at least 10, at least 15 or at least 20.

As mentioned above, it may be desired to provide a neck portion, preferably at a lower part of the elongate element(s), in order to better define the position of at least a major part of the bending.

In one situation, step 2. comprises forming a metallic layer on the tip of the elongated element(s) which has a width at least twice a mean width of the elongated element. In this situation, it may be desired that the metallic layer covers no more than 50% such as 30% of the full length of the elongate element.

In a particularly interesting embodiment, step 1. comprises:
- providing a chamber, preferably airtight, having plasma generating means adapted to generate a plasma and a coil adapted to homogenize the plasma,
- positioning the substrate in relation to, usually below, the coil,
- generating, in the chamber, a plasma comprising a first compound being one or more of the group consisting of $O_2$, $N_2$, Ar and $C_4F8$ and a second compound being one or more of the group consisting of $SF_6$, $CHF_3$, Cl, a halogen based compound, a fluorine based compound and a chlorine based compound, and guiding the plasma toward the substrate while providing power to the coil,
- adjusting or selecting the power fed to the coil to adjust the density of the elongated elements.
- adjusting or selecting a pressure in the chamber to adjust the density of the elongated elements.
- adjusting or selecting a ratio between the first and second compounds to adjust the shape of the elongated elements.
- adjusting or selecting a temperature of 20° C. to −20° C. (preferably about −10° C.) to enable formation of the elongated elements.
- adjusting or selecting an etch time to adjust the height of the elongated elements.

Preferably, the adjusting steps are performed before or shortly after commencing the step of generating and guiding the plasma.

The plasma guiding step may be a providing of a potential/voltage difference between the plasma and the substrate. The potential of the plasma may be controlled or set by the coil or one or more electrodes extending into or being in the vicinity of the plasma. Also, the potential of the substrate may be that of the substrate or an element supporting the substrate.

Preferably, the coil, which may have any desired shape, encircles or outlines an area being larger than that of the substrate in order to obtain a sufficiently homogeneous plasma over the surface of the substrate.

In a preferred embodiment, step 1. comprises a single step of guiding the plasma toward the substrate. Thus, no passivation steps, as are known from the Bosch process, are used. In a passivation step, the plasma is removed and another gas led toward the substrate. So by not having a passivation step, a simpler, cheaper and faster manufacture is obtained.

Preferably, the plasma is guided toward and is allowed to interact with the full surface of the substrate. Thus, no mask is used, as is usual in chip manufacture. This again makes the process cheap and fast.

Preferably, the step of generating and guiding the plasma toward the substrate comprises generating and guiding the plasma toward the substrate for at least 1 minute, such as at least 2, 3, 4, 5, 6, 7, 8, 9 or 10 minutes.

During the generation and directing of the plasma, it may be desired to alter the ratio between the first and second compounds. This alteration may be used for generating a narrowing of the elongated elements to better define a position of bending. More particularly, it may be desired to perform this alteration at a predetermined point in time or within a predetermined period of time, so as to define the position of this narrowing. Usually, this is performed within the last 25%, such as 20%, such as 10% of the time during which the plasma is generated and guided toward the substrate.

In the following, preferred embodiments of the invention will be described with reference to the drawing, in which:

FIG. 1 illustrates substrates according to the invention as well as the leaning mechanism;

FIG. 2 compares Raman spectra of a substrate according to the invention in the leaned and non-leaned configuration to a commercially available substrate;

In general, the present invention relates to a SERS substrate, the manufacture thereof and the use thereof for determining the presence and/or quantity of an analyte. The present substrate in itself will provide advantages compared to commercially available substrates, but especially after having been wetted and subsequently dried, the substrate shows very large improvements. The surface tension of the wetting agent, while evaporating, causes the nanopillars to lean toward each other and form groups of nanopillars which again, by the very large tip density, form hotspots causing the large increase in efficiency.

Figure 1:
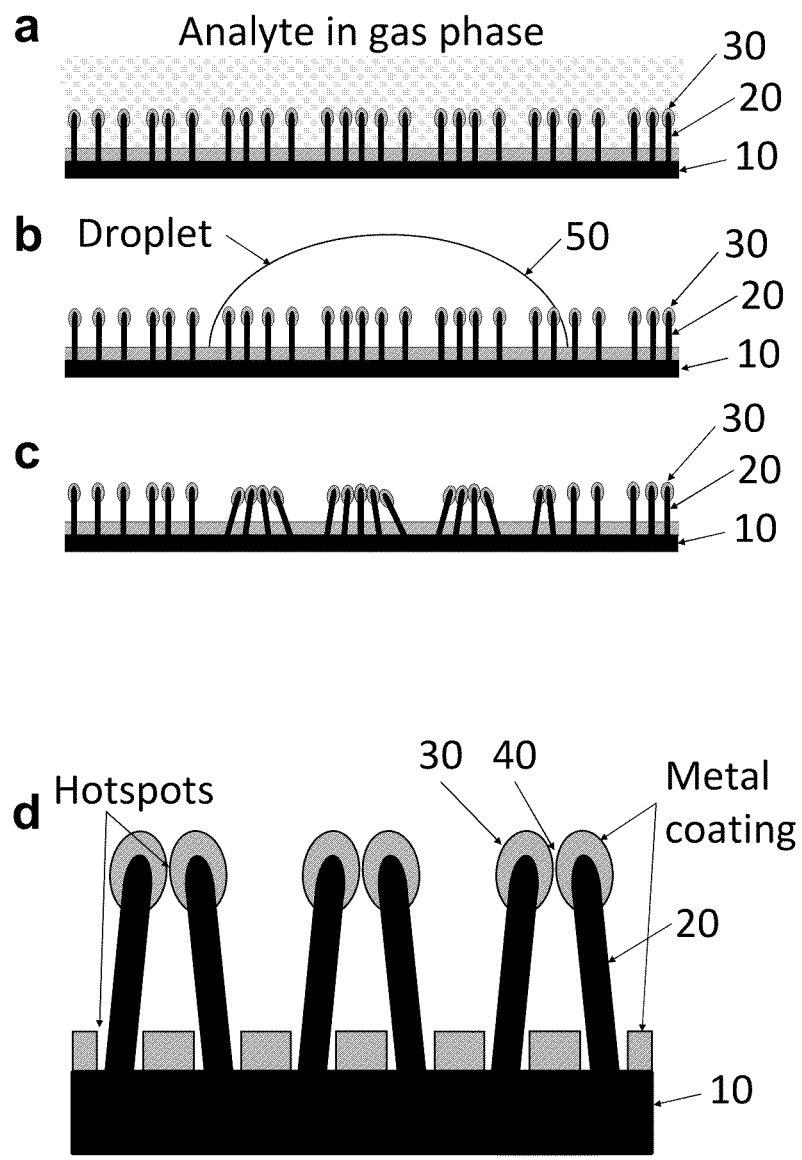
Figure 1:
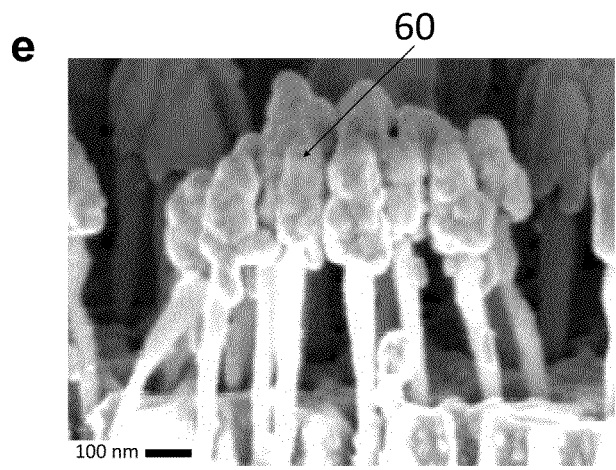
Figure 1:
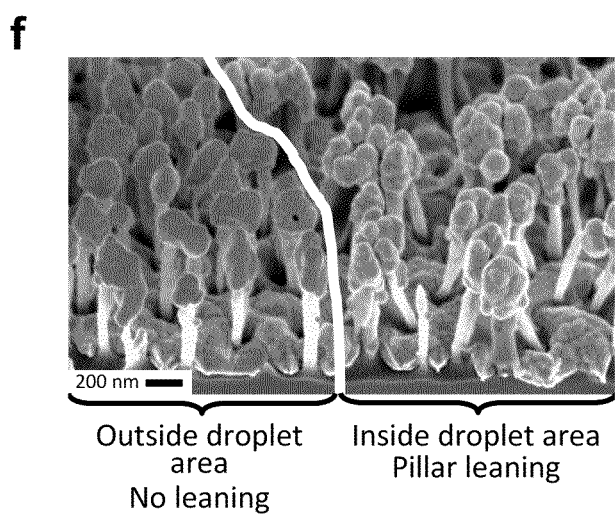
Figure 1:
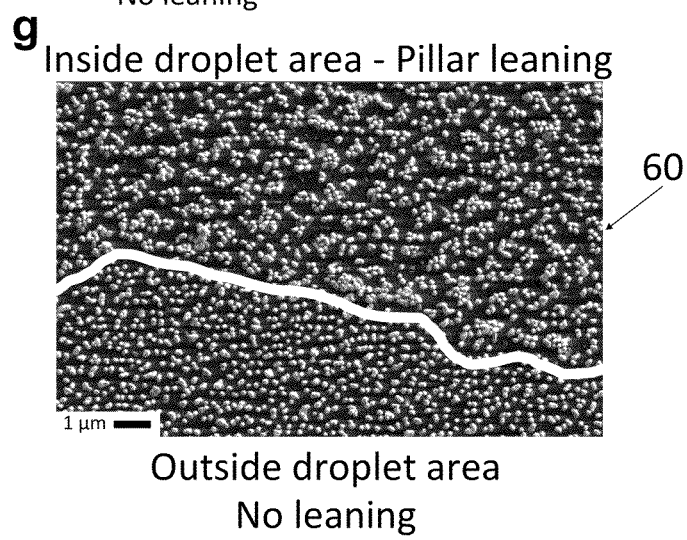

In general, FIG. 1 illustrates, in a)-c) a schematic of the leaning mechanism, which will be described further below. In d), a schematic of the Raman enhancement mechanism is illustrated; when the wetting agent evaporates, surface tension will pull the silicon nanopillars together, trapping the analyte at the hotspot giving rise to a large Raman signal. In e), f) and g), SEM images are provided from 45 degrees and from the top, respectively, of clusters of pillars at the outer perimeter of the evaporated wetting agent droplet area; The nanopillars to the right/upper part have leaned to form clusters/groups which again form hot spots while the nanopillars to the left/lower part remain vertical and free standing. The lines indicate the outer perimeter of the evaporated wetting agent droplet.

In FIG. 1a), a preferred substrate according to the invention is illustrated. This substrate 10 has a plurality of nanopillars 20 each extending away from the substrate 10 and each having a tip 30 which is covered by a SERS active material, such as gold or silver. It is seen that the aspect ratio of the nanopillars 20 is rather large, and that the distance between the nanopillars 20 is sufficient to ensure that metallization thereof coats the individual tips 30 and not merely forms a continuous layer of metal over all tips 30.

In use, when the substrate 10 is exposed to analyte 40 in the gas phase, it is assumed that the analyte adsorbs uniformly all over the silver coated nanopillars 20, including the silver coated tips 30. Raman spectra from the nanopillars exposed to a gaseous analyte 40, such as thiophenol, show an enhancement of the Raman signal on the order of ~$10^8$. This is a 12 times larger Raman enhancement than from a commercially available substrate (Klarite™: Renishaw Diagnostics, http://www.renishawdiagnostics.com/en/12409.aspx) used as a benchmark. Silicon nanopillars 20 coated with gold produce an enhancement half as strong as the silver coated pillars 20 hence a 6 times larger enhancement than the gold coated commercial substrate.

Figure 2:
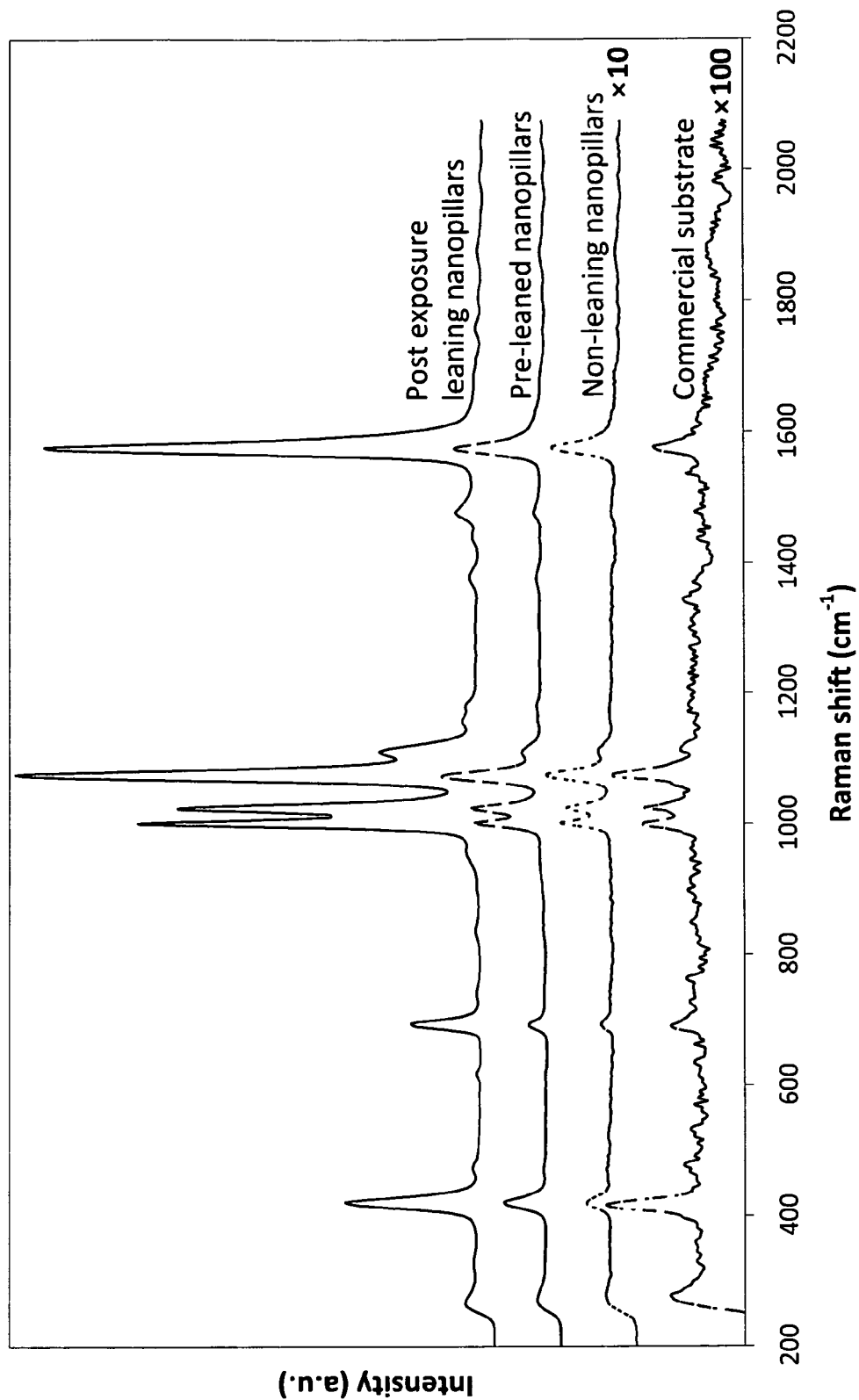

By subsequently depositing a droplet 50 of water or other solvent/liquid onto the substrate 10, see FIG. 1b), and letting it evaporate in e.g. air at room temperature and atmospheric pressure, surface tension will cause the nanopillars 20 to lean toward each other and, see FIG. 1c), thus creating self assembled groups 60 of tips 30 forming hot spots in between. Evaporation at other temperatures and pressures has the same effect as it is the act of evaporation which causes the surface tension to lean the nanopillars 20. As analyte molecules 40 are adsorbed at the tips 30 of the pillars 20, the analyte molecules 40 are thus located also in the hot spots, as the pillars 20 lean toward each other, see FIG. 1d). This self assembling or self grouping mechanism creates a large number of electromagnetic hot spots inside the laser excitation area, drastically increasing the enhancement by a factor of 47 compared to the non-leaning pillars 20 (FIG. 1 a)) just outside the droplet area. Inside the droplet area, the measured Raman enhancement is on the order of $10^9$, as is seen from FIG. 2 illustrating Raman spectra recorded from a silicon nanopillar substrate in both leaning, pre-leaned (see further below) and non-leaning configurations, compared to the commercially available substrate. The substrates were exposed to thiophenol vapour for 60 seconds. The subsequent Raman spectra were recorded with an integration time of 1 second at a laser excitation wavelength of 785 nm. It is clearly seen that the leaning nanopillars create a substantially larger Raman enhancement compared to the non-leaning nanopillars which again provide a better signal than the commercially available substrate.

In the leaning configuration, SEM investigations, see FIG. 1e)-g), show that the distance between the tips 30 of the pillars 20 is very small. However, it can not be ascertained whether actual contact is made. The distance between the tips 30 of the leaning nanopillars 20 is 20 nm or less, such as less than 10 nm, 5 nm or even 3 nm. The nanopillars remain clustered indefinitely, even though it is required that they remain so only until the determination has been completed.

Naturally, other manners than the "evaporating liquid" may be used for obtaining leaning nanopillars and hence groups of tips 30 of nanopillars 20, such as magnetic fields, mechanical vibrations and electrostatic fields. Simply scanning an area of nanopillars with an electron beam as in a scanning electron microscope has been seen to cause nanopillars to lean towards each other due to electrostatic charging. Clearly, the above leaning methods may be used after, as is described above, or before addition of the analyte. In the latter situation, the substrate may be provided in a pre-leaned configuration which already forms the groupings of the tips of nanopillars.

When the pillars are brought to lean prior to analyte exposure, this gives rise to a ~5 times lower enhancement than if the pillars are brought to lean after analyte exposure (FIG. 2).

This is due to the fact that a large portion of the available hotspots in the pre-leaning configuration are not available for analyte adsorbtion.

In addition, the substrate can also be used with a liquid analyte. In this situation, the substrate could be dipped into the analyte solution, or the liquid analyte could simply be deposited onto the substrate and subsequently be allowed to evaporate at any temperature and pressure. When the analyte evaporates, the pillars will lean to again form the hot spots with the analyte molecules trapped in between. The sheer number of formed hot spots makes it very likely that part of the analyte species/molecules will be located in a large number of hot spots which will give rise to a large average Raman signal when excited by the laser source.

Figure 3:
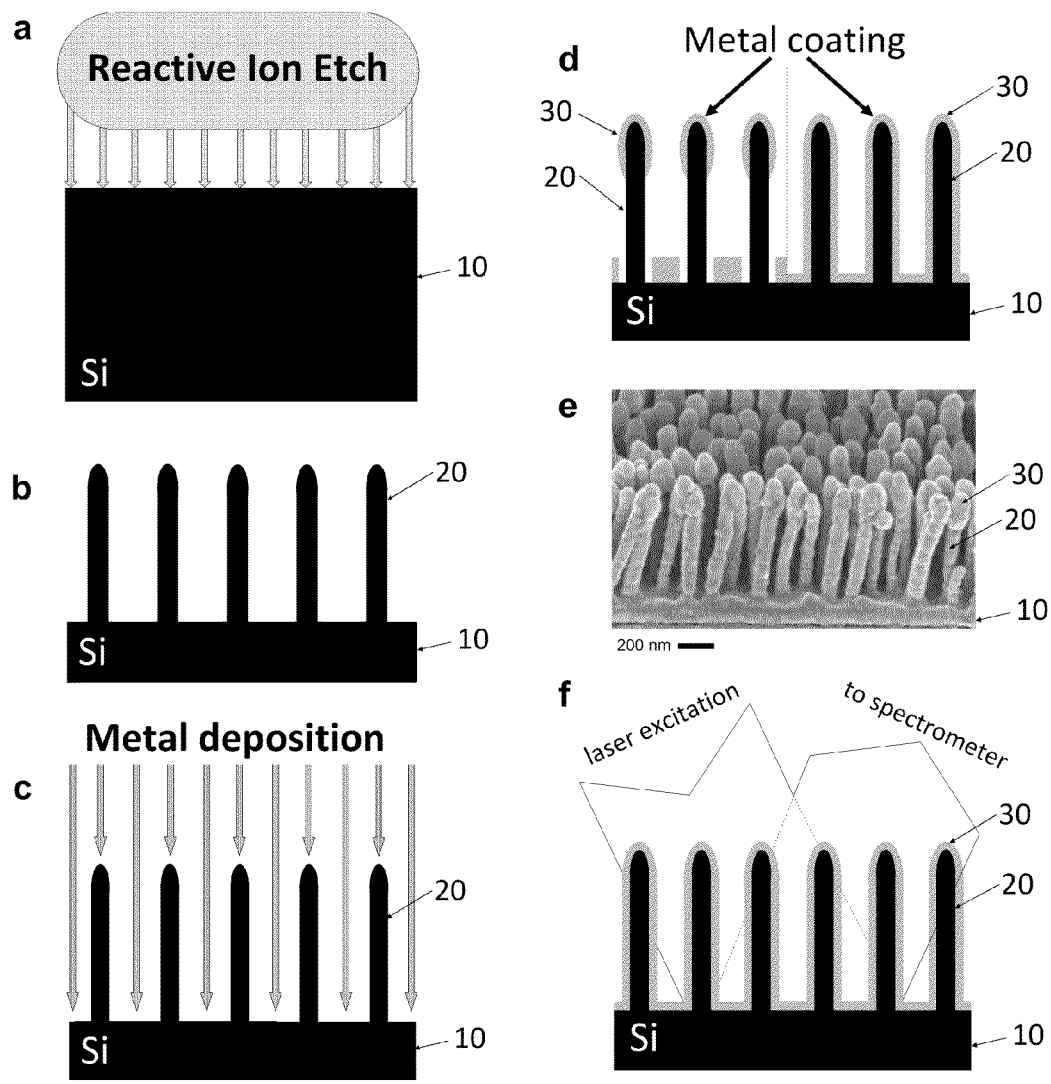
FIG. 3 illustrates the main steps of a preferred manufacture of substrates according to the invention.

The silicon nanopillars 20 may be manufactured using standard silicon processing equipment (Surface Technology Systems MESC Multiplex ICP and Surface Technology Systems Pegasus DRIE have both been used) in a fashion illustrated in FIG. 3, where the main steps are: a) maskless reactive ion etching forms silicon nanopillars 20; b) silver is deposited by either electron beam evaporation or magnetron sputtering onto the silicon nanopillars 20 to form a SERS-active substrate 10. If metallization is performed by magnetron sputtering, the metal layer tends to form a more conformal layer over the length of the nanopillars 20, generating pillars as seen in FIG. 3d), while metallization by electron beam evaporation tends to form lumps at the tips 30 of the silicon pillars, as is seen in FIG. 1e).

By control of process parameters, freestanding high aspect ratio silicon nanopillars with vertical sidewalls and uniform heights can be obtained by maskless reactive ion etching (RIE). The advantage of using a maskless process is two fold: Firstly, it obviously reduces the processing time and ultimately makes the final substrate very cost effective as a consumable substrate. Secondly, producing these small diameter silicon nanopillars (20-100 nm) with the high aspect ratio desired for mechanical leaning would be very challenging using conventional silicon processes including electron beam lithography. In literature the maskless formation of silicon micro- and nanostructures is sometimes referred to as "silicon nanograss" or "black silicon". Silicon nanograss is typically an unwanted side effect in standard silicon processing where its formation is often attributed to micro masking effects caused by re-deposited materials such as photoresist or metal used as masking layers elsewhere on a processed wafer. The process presented here does not rely on such effects. A completely blank wafer is simply inserted into the reactive ion etcher and processed for 3-8 minutes to create the silicon nanopillars in one step.

Figure 7:
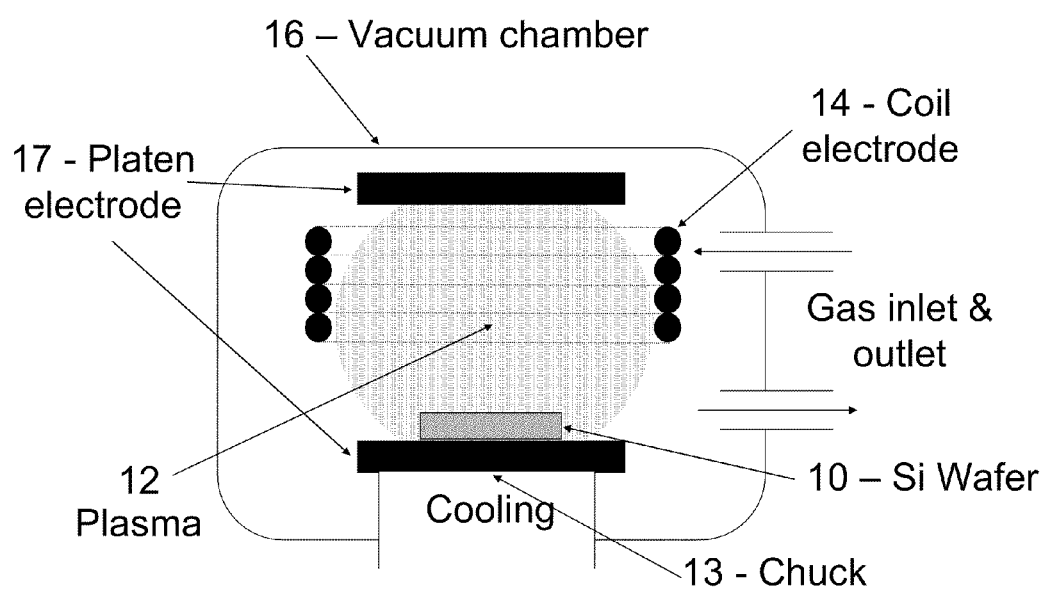
FIG. 7 illustrates the plasma chamber.

A broad variety of nanostructures can be produced by altering the process parameters. In FIG. 7), the main elements of suitable manufacturing equipment is illustrated. The Si substrate 10 is positioned on a wafer chuck 13 and positioned under a coil 14. These elements are positioned in a vacuum chamber 16 and, in operation, the coil 14 operates to generate and homogenize a $O_2$ and $SF_6$ plasma 12 before it is guided toward the substrate 10 by a potential difference applied over the wafer chuck 13 and plasma 12 to form the nanopillars 20. The potential difference may be applied between the wafer chuck 13 and the coil 14 or between the wafer chuck 13 and electrodes 17 which may be provided to extend into the plasma 12.

For SERS substrates, the etching process may be tuned or set-up so that the pillars are e.g. 20-100 nm wide, 600-1600 nm tall and have an aspect ratio on the order of at least 10. The pillar density may be controlled by varying the chamber pressure and/or coil power while the pillar height is simply controlled by the process time.

For silicon nanostructuring, a reactive ion plasma etch (RIE) of undoped 4 inch diameter single side polished single crystal silicon wafers is preferably used. An Advanced Silicon Etcher (Surface Technology Systems MESC Multiplex ICP or Surface Technology Systems Pegasus DRIE) is operated at a temperature of 20° C. to −20° C. with a $SF_6:O_2$ ratio of 1 to 1.12, a platen power of 110-130 W and a chamber pressure of 8 to 56 mTorr and a coil electrode power ranging from 0-150 W. The coil power takes part in the determination of the pillar density. The chamber pressure takes part in the determination of the pillar density. The nanostructured silicon peaks form at a rate of approximately 2 nm/s. The etch time determines the silicon nanopillar height and lies between 3 and 8 minutes.

Subsequent to the formation of the nanopillars, metallization is performed as described further above.

Figure 4:
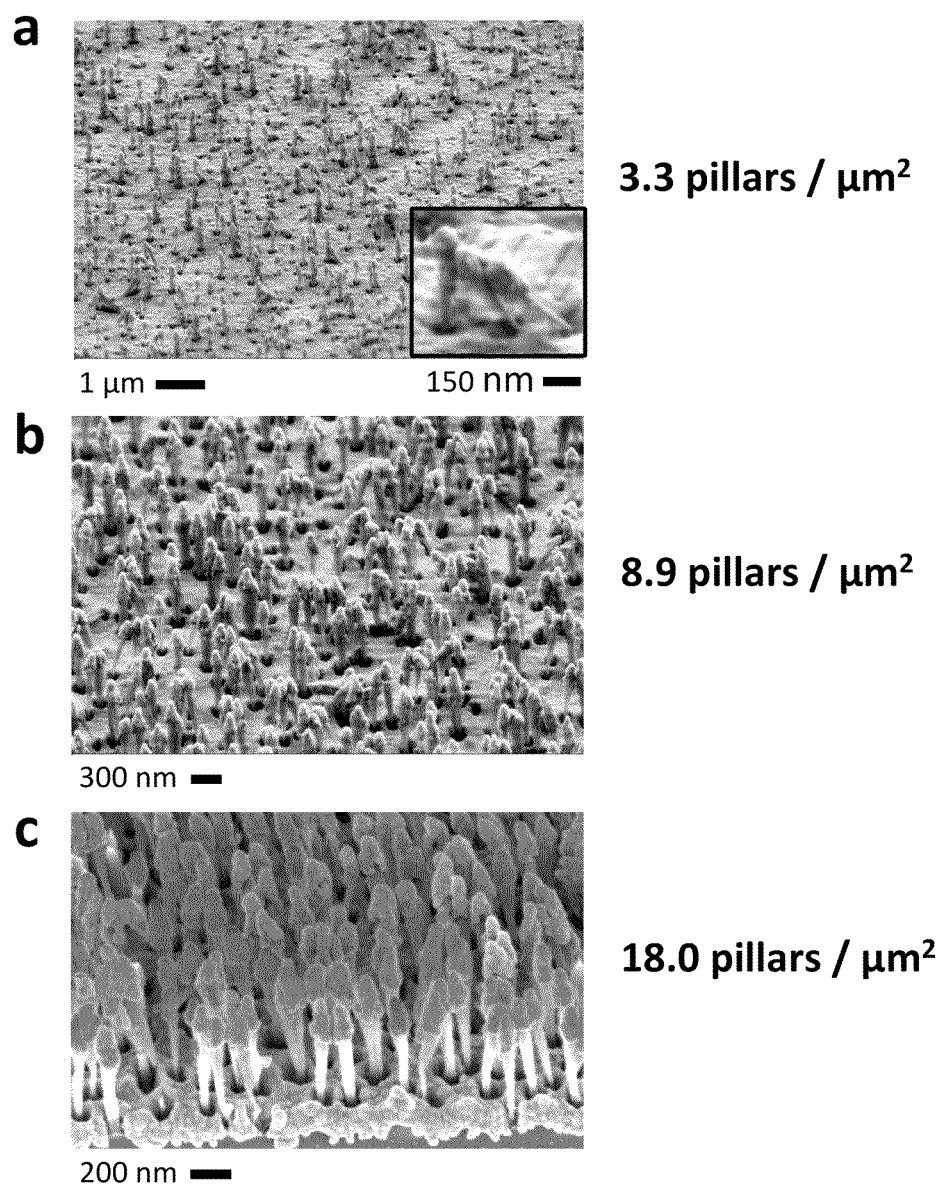
FIG. 4 illustrates the relationship between nanopillar density and Raman enhancement.
Figure 4:
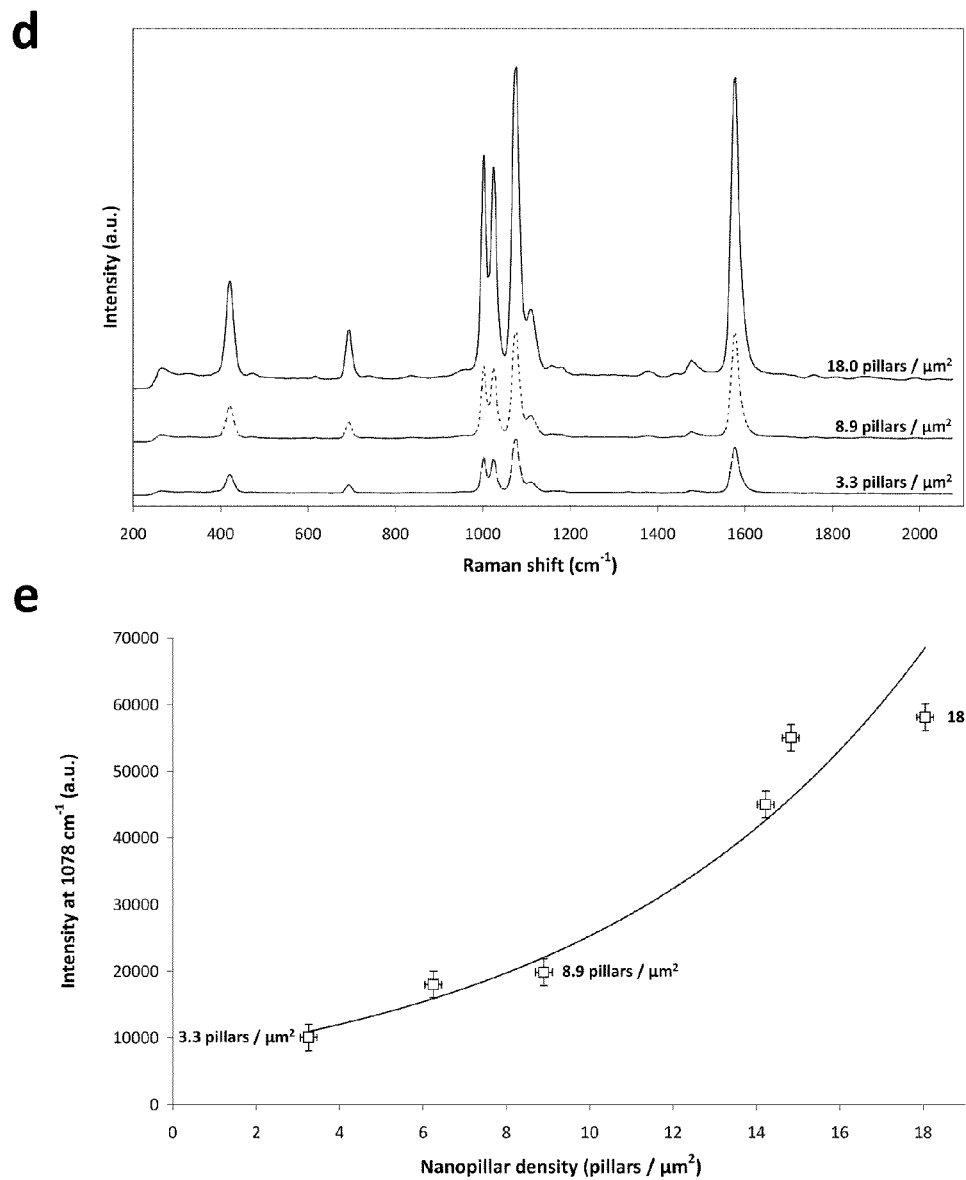

FIG. 4 illustrates substrates with different nanopillar densities obtained by varying the coil power in the plasma chamber 16. The coil power was 100 W, 50 W and 0 W, respectively, in a plasma chamber with a height of 250 mm and diameter of 400 mm. It is seen from the top illustration in FIG. 4a), that despite a relatively low pillar density, the nanopillars will still often lean toward their nearest neighbour(s) to form hot spots. Also, FIG. 4d) illustrates Raman spectra from substrates with the three different nanopillar densities when exposed to thiophenol in the gas phase in the same manner as described in relation to FIG. 2. It is seen from FIG. 4e) that a direct proportional relationship exists between the nanopillar density and Raman enhancement in the leaned configuration.

To prevent contamination in the subsequent SERS spectra, the nanopillars 20 may be manufactured without the fluorocarbon passivation cycles normally used in deep reactive ion etching (the so-called Bosch process). After reactive ion etching, the nano structured silicon may be exposed to an argon and/or oxygen plasma for 1 minute to remove any remnants of the $SF_6$ gas and its decomposition products from the silicon surface. Subsequently the nanopillars 20 are coated with silver by electron beam evaporation (Alcatel SCM 600) to obtain a Raman active surface. By increasing the deposition rate of the evaporating metal (10 Å/s to 60 Å/s) the deposited layer will form elliptical coatings of the silicon nanopillars 20 instead of more spherical shapes. Furthermore, the roughness of the deposited silver layers appears to increase as the deposition rate is increased. The rougher metal coatings yield slightly larger Raman enhancements.

Silver metallization was performed by electron beam evaporation (Alcatel SCM 600) at deposition rates of 10-60 Å/s at a pressure of $2\times10^{-6}$ mbar. The metal layer thickness could be varied with an accuracy of ±5 nm. Magnetron sputtering was performed using a Kurt 3. Lesker CMS 18 system. Sputter rates of 0.16 nm/s were obtained using applied powers of 100 W and a pressure of 2 mTorr.

It is noted that instead of the above-mentioned, preferred $SF_6$, $CHF_3$, Cl or other halogen, fluorine and chlorine based compounds may be used. Also the above-mentioned $O_2$ may be replaced with $C_4F_8$.

Figure 5:
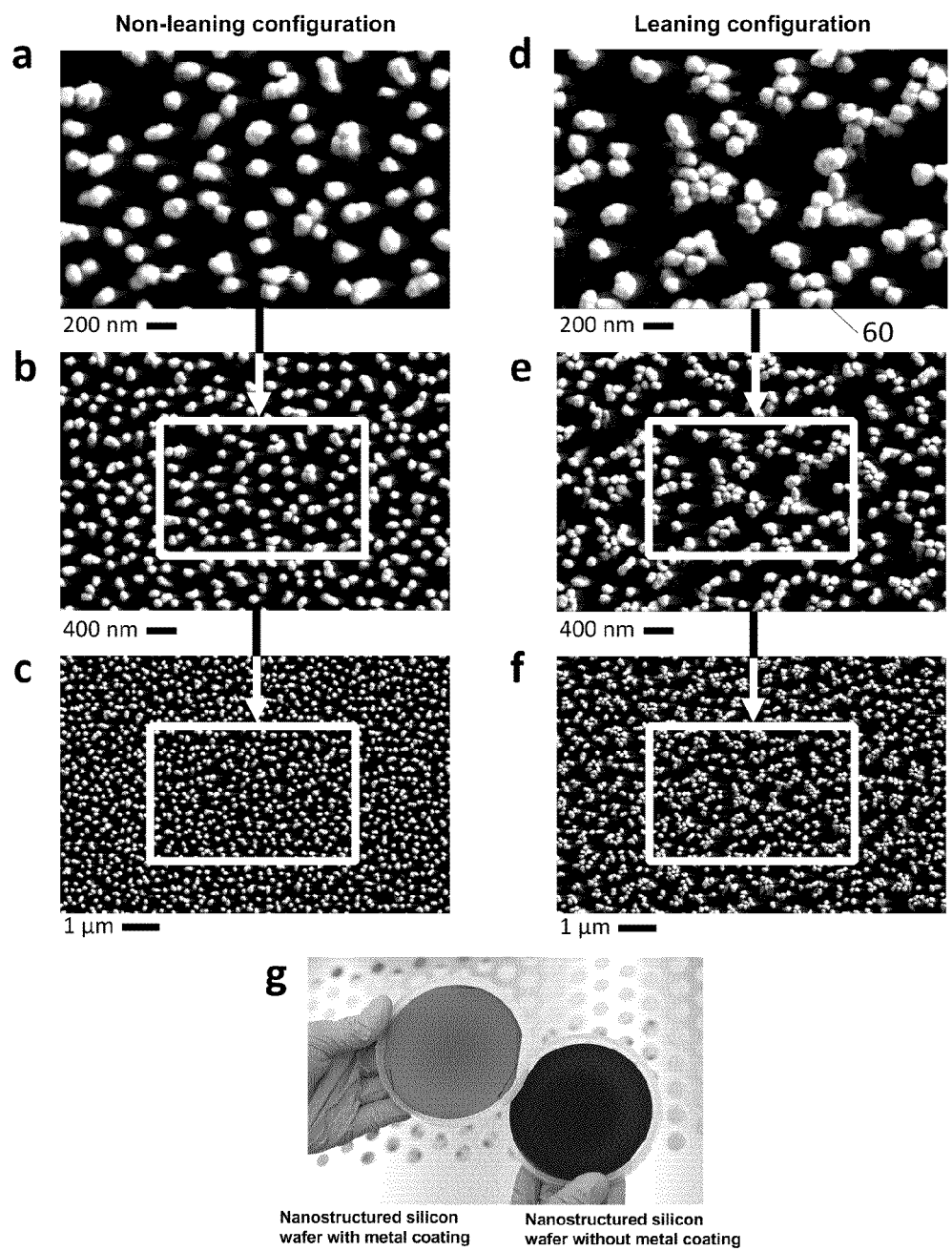
FIG. 5 illustrates the homogeneity of preferred substrates and the possible wafer size.

FIG. 5 illustrates SEM images of different magnifications of a substrate manufactured as described above, using secondary electrons taken at a right angle to the surface. A uniform distribution of metal covered nanopillars is seen over a large area. The etched nanostructure can be repeated over an area of a 4 inch silicon wafer or even larger wafers. Thus, as large areas of these substrates can be produced at a low cost, this will facilitate widespread use of the powerful SERS sensing technique in numerous applications where trace level chemical detection is necessary.

It is clear that the very small tip distance is advantageous for the large Raman enhancement but that it is problematic for metallization. If the pillars were fabricated with a spacing necessary to form hot spots without leaning (distance<5 nm) then metallization of individual nanopillars would be virtually impossible as a continuous silver layer would form on top of the pillars. Thus, leaning of the nanopillars is an advantageous manner of obtaining one without encountering the problem or the other. When the nanopillars 20 can lean, the density of the nanopillars 20 can be tuned to facilitate optimal metallization with respect to the wavelength of the laser to be used for analysis. In addition, the density may be adapted to ensure that the size of the resulting tips also is suitable to the laser or radiation wavelength to be used. The metal tip diameter preferably is significantly smaller than the wavelength of the excitation wavelength. On the other hand, the height of the nanopillars may be adapted to ensure (see further below) that the tips 30 of the bending nanopillars 20 are able to touch or get sufficiently close for the hot spots to form.

Figure 6:
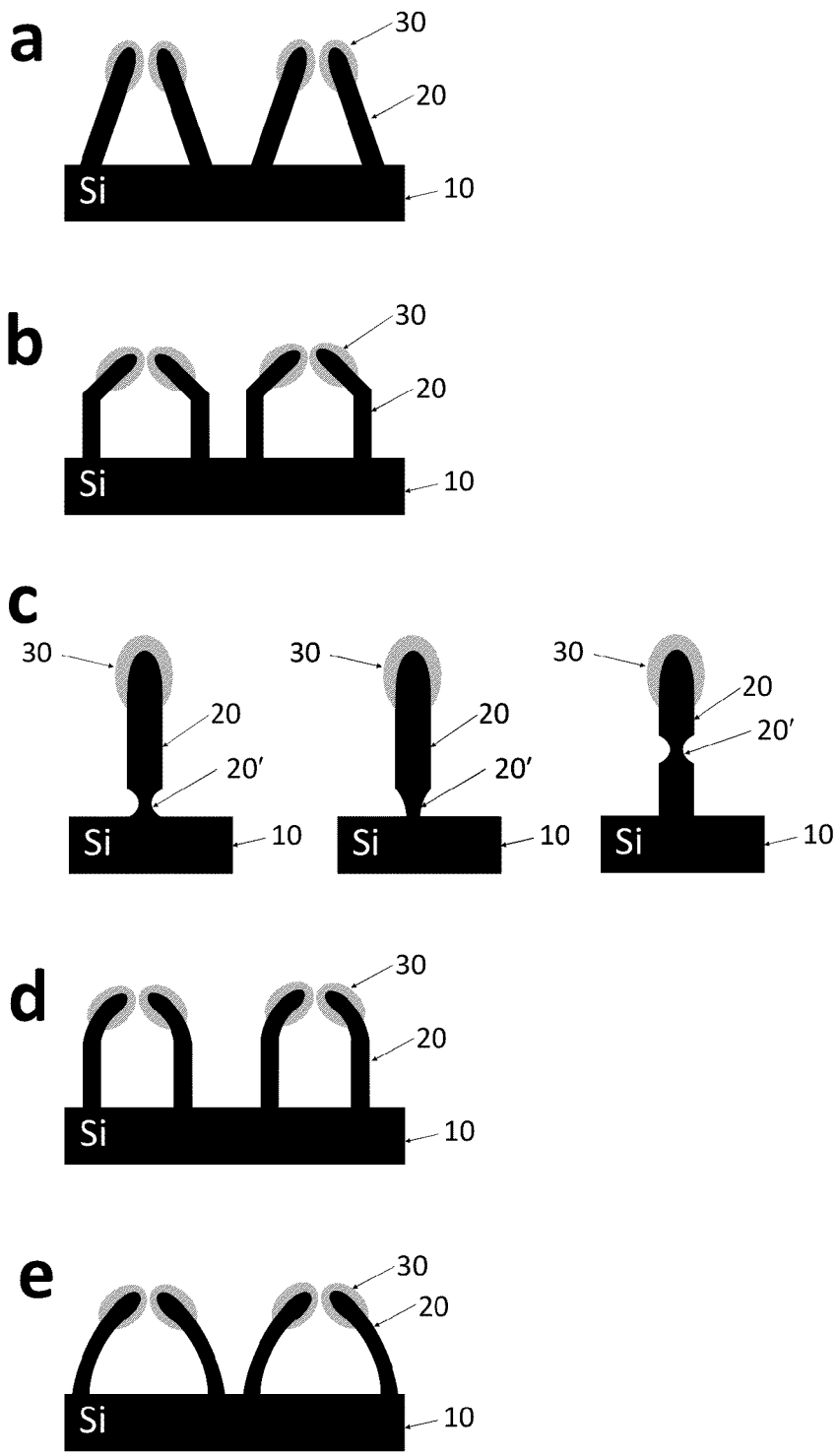
FIG. 6 illustrates different manners of bending of nanopillars.

To obtain leaning and the forming of groups of tips 30, however, the nanopillars 20 should fulfil a number of criteria. Firstly, the dimensions and structure thereof should facilitate the leaning. Thus, the force required to lean the nanopillars 20 should be sufficiently low, whereby the thickness, stiffness and/or modulus thereof should be sufficiently low. Also, the distance between the nanopillars 20 and the actual bending height of the nanopillars 20 should be taken into account, or rather the height of the tip 30 over the bending point of the nanopillar 20, in order to ensure that the tips 30 of the bending nanopillars 20 are able to reach each other. In this respect, the bending point will be the height at which the nanopillar 20 will bend or primarily bend, when a force is exerted at the tip 30 thereof perpendicular to the longitudinal axis of the nanopillar 20. FIG. 6 illustrates, in a) and b) two situations of the same bending angle of two sets of nanopillars 20, where, in a), the pair of nanopillars 20 bend at the substrate 10 and thus have touching or very closely positioned tips 30, whereas, in b), the pair bend about half way along their longitudinal axes and thus must bend much more to still touch, as they are positioned at the same distance at the substrate 10. The situations of a) and b) may be obtained when the bending position along the nanopillar is well defined. In c), such definition is exemplified as a narrowing of the nanopillar at 20'. As described above, this narrowing may be obtained by altering the composition of the plasma, and the position may be defined by the time of altering the composition during the etch time.

In d) and e), nanopillars with a more even width and stiffness are illustrated which therefore bend more evenly.

The determination of a bending point is a standard procedure which requires knowledge of the stiffness/module as well as dimensions of the element. Bending may be at a predetermined point, as would be the case if a neck portion was provided at which the element was weaker and thus most prone to bending. In the present context, the elements or nanopillars normally have a more uniform structure either along most of their length, as would be the situation with the nanopillars 20 of FIG. 3d), or at least between the tip 30 and the substrate 10 (or an upper surface of the metal coating on the substrate if it is deposited up to the nanopillars on the substrate 10; see FIG. 1d)), as would be the situation with the nanopillars 20 in FIG. 1. Naturally, imperfections may occur, whereby the stiffness of the individual nanopillars 20 may differ or vary along their lengths, but the bending point need not be a well-defined point along the longitudinal axis of the nanopillars but more generally a part of the length thereof.

However, the etching process may be tuned to yield silicon nanopillars which are slightly thinner at the very base of the pillar. This thinner point will be the natural point of bending, as illustrated at 20' in FIG. 6c). This tuning may be a increase in the chamber pressure.

The point in time of varying or tuning the etching process to define the bending point 20' may be adapted to other parts of the manufacturing process, as this point in time defines a position, along the length of the nanopillars 20, at which this bending occurs. One situation is one wherein metallization is performed by magnetron sputtering. When relatively thick layers of silver are deposited by this method, the base of the pillars also tends to be covered. Then, it may be desired to define a longer nanopillar, along the longitudinal direction of the nanopillar, are of reduced thickness of the metal, or a more reduced thickness to ensure that the bending is still performed at this position in spite of the metal layer.

In general, the metalized nanopillars preferably are manufactured to have a uniform height, which on the one side eases the task of focusing the excitation laser since the depth of field is much larger than the height differences of the pillars. Furthermore it is advantageous that the nanopillars have a uniform height for the tips 30 to, in the bent configuration, to be sufficiently close to form the groups 60 and the hot spots.

The cavities in the silver layer (evaporation deposited) formed at the base of the pillars lead to additional hot spots which, however to a much lower degree, contribute to the Raman signal, see FIG. 1d).

Thus, the preferred SERS substrate has nano scale metal features with well controlled size, shape, location, and orientation. A simple two step process may be used for manufacturing wafer scale areas of uniform SERS substrate with exceptionally large Raman enhancement) ($10^9$-$10^{10}$. These substrates can be stored until needed (Ag in a protective atmosphere) and can be employed for both liquid and gas phase detection for various chemical and biochemical applications. A particular advantage is that the nanopillars may be brought to lean toward each other to self assemble into groups forming hot spots responsible for an exceptionally large Raman enhancement. Furthermore, this technique opens up for the possibility to tune the size of the silver coatings on the tips 30 of the silicon pillars 20 to optimally absorb the excitation laser light of any given wavelength.

The invention claimed is:

1. A substrate, comprising:
   a base; and
   a plurality of elongated elements extending from the base, each elongated element having a tip positioned at one end away from the base, at least one tip having a metallic surface, the elongated elements being positioned, at the base, with a density of at least $1 \times 10^8$ elongated elements per $cm^2$,
   wherein each elongated element has a neck portion and a tip portion, the tip portion being positioned at the tip and having a larger cross section, perpendicular to a longitudinal direction of the elongated elements, than the neck portion which is positioned closer to the base than the tip portion, a mean width of the neck portion being no more than 80% of a mean width of the tip portion.

2. A substrate according to claim 1, wherein each elongated element has a height, along the longitudinal direction thereof, of at least 30 nm.

3. A substrate according to claim 1, wherein each elongated element has a height being at least 2 times a mean spacing between the elongated elements.

4. A substrate according to claim 1, wherein a majority of the elongated elements have a height within 20% of a mean height of the majority of the elongated elements.

5. A substrate according to claim 1, wherein each elongated element has a ratio between a height along the longitudinal direction thereof and a mean width thereof of at least 5.

6. A substrate according to claim 1, wherein each of the elongated elements is a silicon element.

7. A substrate according to claim 1, wherein at least one elongated element has a spring constant of no more than 250 N/m.

8. A substrate, comprising:
   a base; and
   a plurality of elongated elements extending from the base, each elongated element having a tip positioned at one end away from the base, at least one tip having a metallic surface, the elongated elements being positioned at the base, with a density of at least $1 \times 10^8$ elongated elements per $cm^2$,
   wherein at least one elongated element is bendable by providing a force to the tip thereof, the force being of no more than 20 µN and being perpendicular to the longitudinal direction of the at least one elongated element such that the tip moves at least 50% of a height of the elongated element along the longitudinal direction.

9. A substrate according to claim 1, wherein at least 25% of the elongated elements form part of a group with at least 3 elongated elements.

10. A method of transforming the substrate of claim 1, the method comprising:
    providing the substrate including the base and the plurality of elongated elements, the elongated elements having metallized tips and extending from the base in at least a substantially same direction; and
    forming a plurality of groups of the elongated elements, the tips of the elongated elements of each group being positioned within a distance of 5 nm or less from each other.

11. A method according to claim 10, wherein the forming the plurality of groups includes humidifying with a liquid and subsequently drying the elongated elements.

12. A method according to claim 10, wherein the forming the plurality of groups includes exerting a force to the substrate and causing adhesion of the tips to each other by surface tension, electrostatic or magnetic forces.

13. A method of detecting the presence of a substance on a surface of the substrate according to claim 8, the method comprising:
    providing radiation toward the tips and performing Raman Spectroscopy on the basis of radiation inelastically scattered by the substance.

14. A method according to claim 13, further comprising:
    estimating a quantity of the substance present on the substrate on the basis of a received intensity of scattered radiation having a wavelength within one or more predetermined wavelength intervals.

15. A method for producing a substrate, the method comprising:
    providing, in or on the substrate, a plurality of elongated elements extending from a surface of the substrate, each elongated element having a tip positioned at one end away from the surface, the elongated elements being positioned, at the surface, with a density of at least $1 \times 10^8$ elongated elements per $cm^2$,
    providing a metallic surface having a thickness of at least 5 nm on at least a tip of one of the elongated elements, and
    providing groups of two or more of the elongated elements, the tips of the elongated elements of each group having a distance between one another of less than or equal to 5 nm.

16. A method according to claim 15, wherein the providing the plurality of elongated elements includes providing elements with a height, along a longitudinal direction thereof, of at least 30 nm.

17. A method according to claim 15, wherein the providing the plurality of elongated elements includes providing a majority of the elongated elements with a height within 20% of a mean height of the majority of the elongated elements.

18. A method according to claim 15, wherein the providing the plurality of elongated elements includes providing at least one elongated element with a ratio between a height along a longitudinal direction thereof and a mean width thereof of at least 5.

19. A method according to claim 15, the providing the groups includes forming a metallic layer on the tip of the elongated element which has a width at least twice a mean width of the elongated element.

20. A method of forming a substrate, comprising:
providing a base; and
providing a plurality of elongated elements extending from the base, each elongated element having a tip positioned at one end away from the base, at least one tip having a metallic surface, the elongated elements being positioned, at the base, with a density of at least $1 \times 10^8$ elongated elements per $cm^2$, wherein the providing a plurality of elongated elements includes,
providing a chamber having a plasma generator configured to generate a plasma and a coil configured to homogenize the plasma,
positioning the substrate below the coil,
generating, in the chamber, a plasma comprising a first compound being one or more of the group consisting of $O_2$, $N_2$, Ar and $C_4F_8$ and a second compound being one or more of the group consisting of $SF_6$, $CHF_3$, Cl, a halogen based compound, a fluorine based compound and a chlorine based compound, and guiding the plasma toward the substrate while providing power to the coil,
adjusting the power fed to the coil to adjust the density of the elongated elements,
adjusting the pressure in the chamber to adjust the density of the elongated elements,
adjusting the ratio between the first and second compounds to adjust the shape of the elongated elements, and
adjusting the temperature to enable formation of the elongated elements.

21. A method according to claim 20, wherein the providing the plurality of elongated elements includes a single step of guiding the plasma toward the substrate controlled by a set platen power.

22. A method according to claim 20, wherein the generating and guiding the plasma toward the substrate includes generating and guiding the plasma toward the substrate for at least 1 minute controlled by a set platen power.

23. A method of detecting the presence of a substance on a surface of the substrate transformed according to claim 10, the method comprising:
providing radiation toward the tips and performing Raman Spectroscopy on the basis of radiation inelastically scattered by the substance.

24. A method according to claim 23, further comprising:
estimating a quantity of the substance present on the substrate on the basis of a received intensity of scattered radiation having a wavelength within one or more predetermined wavelength intervals.

25. A substrate according to claim 1, wherein the base and the elongated elements are made of the same material.

26. A method according to claim 15, wherein the base and elongated elements are made of the same material.

27. A substrate according to claim 1, wherein the elongated elements are positioned, on the substrate, with a density of less than $4 \times 10^9$ tips per $cm^2$.

28. A substrate according to claim 1 wherein the elongated elements are perpendicular to a plane of the base.

29. A method according to claim 10, wherein the forming the groups comprises bending the elongated elements of the groups.

30. A method according to claim 15, wherein each of the elongated elements is a silicon element.

* * * * *

UNITED STATES PATENT AND TRADEMARK OFFICE
CERTIFICATE OF CORRECTION

PATENT NO. : 8,767,202 B2  Page 1 of 1
APPLICATION NO. : 12/911061
DATED : July 1, 2014
INVENTOR(S) : Michael Stenbaek Schmidt, Anja Boisen and Jörg Hübner It is certified that error appears in the above-identified patent and that said Letters Patent is hereby corrected as shown below:

Title Page, Item (56), U.S. PATENT DOCUMENTS, insert:

--7,940,387 B2 *   05/10/2011   Dluhy et al.--

Signed and Sealed this
Twenty-seventh Day of January, 2015

Michelle K. Lee
*Deputy Director of the United States Patent and Trademark Office*